United States Patent

Baumgarth et al.

[11] 4,264,584
[45] Apr. 28, 1981

[54] HYDROCORTISONE ORTHOESTERS, PHARMACEUTICAL FORMULATIONS THEREOF AND PROCESSES FOR THE PREPARATION THEREOF

[75] Inventors: Manfred Baumgarth; Dieter Orth; Jürgen Harting, all of Darmstadt, Fed. Rep. of Germany; Hans Schaefer, Antibes, France; Achim Zesch, Berlin, Fed. Rep. of Germany

[73] Assignee: Merck Patent Gesellschaft mit Beschrankter, Darmstadt, Fed. Rep. of Germany

[21] Appl. No.: 92,911

[22] Filed: Nov. 9, 1979

[30] Foreign Application Priority Data

Nov. 9, 1978 [DE] Fed. Rep. of Germany ....... 2848584

[51] Int. Cl.³ ............................................. C07J 71/00
[52] U.S. Cl. ........................... 424/241; 260/239.55 R; 260/239.55 D
[58] Field of Search ............. 260/239.55 D, 239.55 R; 424/241

[56] References Cited

U.S. PATENT DOCUMENTS

| | | | |
|---|---|---|---|
| 3,147,249 | 9/1964 | Ercoli et al. | 260/239.55 |
| 3,716,529 | 2/1973 | Ackrell et al. | 260/239.55 D |
| 3,798,217 | 3/1974 | Ackrell et al. | 260/239.55 |

*Primary Examiner*—Elbert L. Roberts
*Attorney, Agent, or Firm*—Millen & White

[57] ABSTRACT

Hydrocortisone orthoesters of the formula

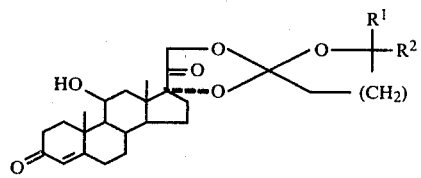

wherein $R^1$ and $R^2$ are independently each H or $CH_3$ and n is 1 or 2 possess antiphlogistic activity.

10 Claims, No Drawings

HYDROCORTISONE ORTHOESTERS, PHARMACEUTICAL FORMULATIONS THEREOF AND PROCESSES FOR THE PREPARATION THEREOF

The present invention relates to new hydrocortisone orthoesters.

SUMMARY OF THE INVENTION

It is an object of this invention to provide new compounds having valuable properties, especially those which can be used for the preparation of medicaments.

Upon further study of the specification and appended claims, further objects and advantages of this invention will become apparent to those skilled in the art.

These objects have been achieved by providing compounds of Formula I

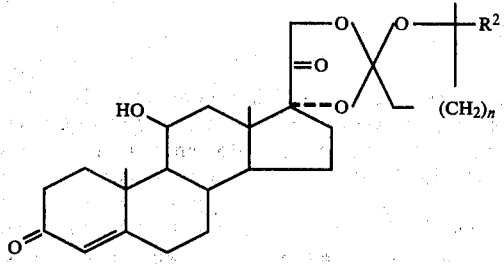

in which $R^1$ and $R^2$ are independently H or $CH_3$ and n is 1 or 2.

DETAILED DISCUSSION

In Formula I, $R^1$ and $R^2$ are preferably H; and the parameter n preferably is 2. Accordingly, the invention relates in particular to those compounds of Formula I in which at least one of $R^1$ and $R^2$ and/or the parameter n have one of these preferred meanings.

The present invention also relates to a process for the preparation of the compounds of Formula I, comprising reacting hydrocortisone with a lactone of Formula II

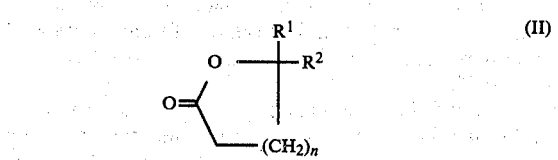

wherein $R^1$, $R^2$ and n are as defined above, or with a reactive derivative thereof.

In other respects, the hydrocortisone orthoesters of Formula I are prepared by methods which are in themselves known, such as those described in the literature (for example, in the standard works such as Houben-Weyl, Methoden der organischen Chemie (Methods of Organic Chemistry), Georg-Thieme-Verlag, Stuttgart; and also, for example, German Offenlegungsschrift No. 2,122,351), and in particular are prepared under reaction conditions which are known and suitable for these reactions. It is also possible to make use of variants which are in themselves known and are not mentioned in more detail herein.

Suitable reactive derivatives of the lactones of Formula II which can be used include preferably the corresponding lactone acetals of Formula III

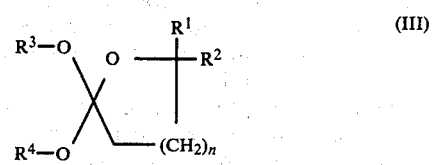

in which $R^3$ and $R^4$ in each case are alkyl of 1-4 carbon atoms or together are $-C_mH_{2m}-$ and m is 2, 3 or 4, and $R^1$, $R^2$ and n are as defined above, and also lactonium salts of Formula IV

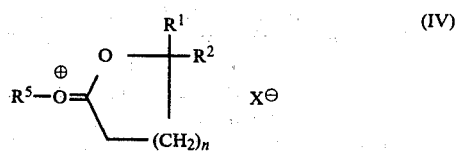

in which $R^5$ is alkyl of 1-4 carbon atoms and $X^\ominus$ is an anion, such as $BF_4^\ominus$ or $SbF_6^\ominus$, and $R^1$, $R^2$ and n are as defined above.

In the lactone derivatives of Formulae III and IV, $R^3$, $R^4$ and $R^5$ are preferably methyl or ethyl; $R^3$ and $R^4$ together are also preferably $-CH_2CH_2-$ or $-CH_2CH_2CH_2-$, but also propyl, isopropyl, butyl, isobutyl or sec-butyl; or $R^3$ and $R^4$ together are also $-CH_2CH_2CH_2CH_2-$, $-CH_2-CH(CH_3)-$, $-CH(CH_3)-CH(CH_3)-$, $-CH_2-CH(C_2H_5)-$ and the like.

Some of the starting materials of the Formulae III and IV are known. (See, for example, Chem. Ber. 89, 2060-2079 (1956) and J. Org. Chem. 42, 3207 (1977).) The compounds of Formulae III and IV which are not known can be prepared analogously to the known compounds by processes which are in themselves known. If desired, the starting materials can also be prepared in situ, in such a way that they are not isolated from the reaction mixture but are immediately further reacted to yield compounds of Formula I.

The orthoesters of Formula I can be prepared by reacting hydrocortisone with lactones of Formula II, but are preferably prepared by reacting hydrocortisone with lactone acetals of Formula III.

The reaction of hydrocortisone with the lactone acetals III is preferably carried out in an inert organic solvent, preferentially in amides, such as dimethylformamide, dimethylacetamide or formamide, sulfoxides, such as dimethylsulfoxide, or nitriles, such as acetonitrile; at temperatures of 0°-150° C. and preferably 100°-120° C.; in the presence of an acid catalyst, for example, a mineral acid, such as hydrochloric acid or sulfuric acid, a sulfonic acid, such as p-toluenesulfonic acid, or a Lewis acid, such as $BF_3$ or $AlCl_3$. An excess of the lactone acetal III is also suitable as the solvent.

The reaction of hydrocortisone with the lactonium salts IV is preferably likewise effected in the presence of an inert organic solvent or suspending agent, for example, a halogenated hydrocarbon, such as chloroform, methylene chloride, carbon tetrachloride or 1,2- or 1,1-dichloroethane, a hydrocarbon, such as benzene or toluene, or an ether, such as diethyl ether or dioxane; in the presence of a base, such as ammonia, triethylamine or pyridine; and at temperatures of about 0°–50° C.

It has been found that the compounds of Formula I possess valuable pharmacological properties coupled with good tolerance. In particular, they display antiphlogistic activity which can be ascribed, for example, to an antiproliferative active component (detectable, for example, analogously to the method of Rudas, Drug Research 10, 226 (1969)), an antiexsudative active component (detectable, for example, analogously to the method described by Hotovy and Kapff, Arch. Int. Pharmacodyn., 111, 420–436 (1957); granuloma pouch test), a thymolytic active component (detectable, for example, analogously to the method of Steelman et al, Steroids 1, 163 (1963)) and an active component which influences the ACTH (detectable on the basis of the inhibition of an adrenal hypertrophy analogously to the method of Bohus, B., Acta Physiol. Acad. Sci. Hung. 29, 203 (1966)). Therefore, the compounds of Formula I are suitable, for example, for combating persistent allergies and other inflammatory diseases of the skin, and also for the treatment of rheumatoid arthritis. These activities are detectable by test methods conventional for this purpose.

The compounds of Formula I can therefore be used as medicinally active compounds to treat patients in human medicine and veterinary medicine, e.g., mammals, and also as intermediate products for the preparation of other medicinally active compounds.

Thus, this invention also relates to the use of the new compounds of Formula I for the preparation of pharmaceutical formulations, especially by a non-chemical route. The compounds I can be brought into a suitable dosage form together with at least one solid, liquid and/or semi-liquid excipient or auxiliary and optionally in combination with one or more additional active compounds.

The invention also relates to agents, especially pharmaceutical formulations, containing at least one compound of Formula I.

These formulations can be used as medicaments in human medicine and in veterinary medicine. Excipients which can be used include organic or inorganic substances which are particularly suitable for topical application and do not react with the new compounds, for example, water, vegetable oils, hydrocarbons such as alkylated naphthalenes, halogenated hydrocarbons such as $CF_2Cl_2$ (for example, for aerosols), benzyl alcohols, polyethylene glycols, glycerol triacetate, gelatin, carbohydrates, such as lactose or starch, magnesium stearate, talc and petroleum jelly. The formulations used for topical application include, in particular, solutions, lotions, emulsions, sprays (aerosols), ointments, creams, pastes or powders. The new compounds can also be lyophilized. The indicated formulations can be sterilized and/or contain auxiliaries such as lubricants, preservatives, stabilizers and/or wetting agents, emulsifiers, salts for influencing the osmotic pressure, buffer substances, dyes and/or aroma generating substances. They can, if desired, also contain one or more additional active compounds, for example, one or more antibiotics, such as gentamycin, and/or antimycotics and/or other substances having a topical action.

The new compounds are as a rule administered analogously to known anti-inflammatory agents available commercially (for example, hydrocortisone 17-butyrate). In the case of topical application in combination with excipients suitable for this purpose, a good activity can be determined over relatively wide dilution ranges. For example, concentrations of the active compound of about 0.05–1 percent by weight, based on the weight of the preparation, are effective for healing inflammations. Concentrations of about 0.01 to 0.5 percent by weight are preferred.

For oral or parenteral administration, the daily dosage is generally about 0.01 to 1 mg/kg of body weight. Unit dosages are about 0.5 to 50 mg; preferably 5 to 25 mg.

Each of the compounds of Formula I named in the examples which follow is particularly suitable for the preparation of pharmaceutical formulations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A mixture of 36.25 g of hydrocortisone, 36 ml of 2,2-diethoxytetrahydrofuran, 36 ml of dry dimethylformamide and 150 mg of p-toluenesulfonic acid is stirred at 115° for 3 hours and then cooled; 1.2 ml of pyridine is added; and the resulting mixture is poured into water. The mixture is extracted with methylene chloride and the extract is washed with water, dried over sodium sulfate and evaporated. After purification by chromatography (silica gel; methylene chloride/petroleum ether/acetone 5:5:2+0.1% of triethylamine), 17α,21-tetrahydrofuranylidene-2′,2′-dioxy-4-pregnen-11β-ol-3,20-dione is obtained; melting point 223°–225° (from acetone); $[\alpha]_D^{20}+120.4°$ (chloroform).

EXAMPLES 2 TO 6

The following compounds are obtained analogously to EXAMPLE 1 from hydrocortisone and 2,2-diethoxy-5-methyltetrahydrofuran (boiling point 71°–72°/14 mm), 2,2-diethoxy-5,5-dimethyl-tetrahydrofuran (boiling point 72°–75°/14 mm), 2,2-diethoxytetrahydropyran, 6-methyl-2,2-diethoxytetrahydropyran or 6,6-dimethyl-2,2-diethoxy-tetrahydropyran:

2. 5′-Methyl-17α,21-tetrahydrofuranylidene-2′,2′-dioxy-4-pregnen-11β-ol-3,20-dione, melting point 190°–192°.

3. 5′,5′-Dimethyl-17α,21-tetrahydrofuranylidene-2′,2′-dioxy-4-pregnen-11β-ol-3,20-dione, melting point 143°–145° and 185°–186° (two crystal modifications); $[\alpha]_D^{20}+105°$ (chloroform).

4. 17α,21-Tetrahydropyranylidene-2′,2′-dioxy-4-pregnen-11β-ol-3,20-dione, melting point 234°–236°; $[\alpha]_D^{20}+104.4°$ (chloroform).

5. 6′-Methyl-17α,21-tetrahydropyranylidene-2′,2′-dioxy-4-pregnen-11β-ol-3,20-dione.

6. 6′,6′-Dimethyl-17α,21-tetrahydropyranylidene-2′,2′-dioxy-4-pregnen-11β-ol-3,20-dione.

EXAMPLE 7

The product described in EXAMPLE 4 is obtained analogously to EXAMPLE 1 from hydrocortisone and 2,2-ethylenedioxy-tetrahydropyran (boiling point 73°–76°/12 mm) or 2,2-(propylene-1,3-dioxy)-tetrahydropyran (boiling point 87°–89°/14 mm).

EXAMPLE 8

1 g of triethyloxonium tetrafluoborate is dispersed in 5 ml of dry methylene chloride under $N_2$, 0.45 ml of butyrolactone is added and the mixture is left to stand overnight at 25°. 1.6 ml of the O-ethylbutyrolactonium tetrafluoborate solution thus obtained is then added dropwise over the course of 15 minutes at 25°, with stirring, to a dispersion of 362 mg of hydrocortisone in a solution of 200 mg of triethylamine in 18 ml of dry methylene chloride. The resulting mixture is filtered through $Al_2O_3$. 17α,21-Tetrahydrofuranylidene-2',2'-dioxy-4-pregnen-11β-ol-3,20-dione with a melting point of 223°–225° is obtained from the filtrate.

The examples which follow relate to pharmaceutical formulations which contain compounds of the Formula I (percentages are percentages by weight).

EXAMPLE A: OINTMENT

| | |
|---|---|
| 17α,21-Tetrahydropyranylidene-2',2'-dioxy-4-pregnen-11β-ol-3,20-dione | 0.25% |
| Anhydrous wool fat | 2.0% |
| Viscous paraffin | 10.0% |
| White petroleum jelly | to make up to 100.0% |

EXAMPLE B: CREAM

| | |
|---|---|
| 17α,21-Tetrahydropyranylidene-2',2'-dioxy-4-pregnen-11β-ol-3,20-dione | 0.5% |
| Cetyl alcohol | 9.0% |
| Viscous paraffin | 3.0% |
| Glycerol monostearate | 2.0% |
| Propylene glycol monostearate | 2.0% |
| Glycerol | 2.0% |
| Very finely divided silica | 0.1% |
| Petroleum jelly | 10.0% |
| Polyoxyethylenesorbitane monopalmitate | 30.0% |
| Methyl p-hydroxybenzoate | 0.065% |
| Propyl p-hydroxybenzoate | 0.035% |
| Propylene glycol | 3.0% |
| Water | to make up to 100.0% |

EXAMPLE C: LOTION

| | |
|---|---|
| 17α,21-Tetrahydropyranylidene-2',2'-dioxy-4-pregnen-11β-ol-3,20-dione | 0.2% |
| Viscous paraffin oil | 10.0% |
| Ethanol | 2.0% |
| Glycerol | 1.0% |
| Propylene glycol | 2.0% |
| Sorbic acid | 0.15% |
| Fatty alcohol polyglycol ether | 2.0% |
| Mixture of cetylstearyl alcohol and sodium cetylstearyl sulfate and a non-ionic emulsifier | 0.5% |
| Perfume oil of lily-of-the-valley | 0.01% |
| Water | to make up to 100.0% |

EXAMPLE D: OINTMENT

| | |
|---|---|
| 17α,21-Tetrahydropyranylidene-2',2'-dioxy-4-pregnen-11β-ol-3,20-dione | 0.1% |
| Gentamycin sulfate (based on free gentamycin base) | 0.1% |
| Cetyl alcohol | 2.4% |
| Andhydrous wool fat | 1.0% |
| Viscous paraffin | 15.0% |
| White petroleum jelly | to make up to 100.0% |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hydrocortisone orthoester of the formula

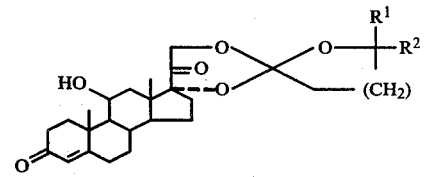

wherein $R^1$ and $R^2$ are independently each H or $CH_3$ and n is 1 or 2.

2. A compound of claim 1, wherein $R^1$ and $R^2$ are H.

3. A compound of claim 1, wherein n is 2.

4. 17α,21-Tetrahydrofuranylidene-2',2'-dioxy-4-pregene-11β-ol-3,20-dione, a compound of claim 1.

5. 5'-Methyl-17α,21-tetrahydrofuranylidene-2',2'-dioxy-4-pregnen-11β-ol-3,20-dione, a compound of claim 1.

6. 5',5'-Dimethyl-17α,21-tetrahydrofuranylidene-2',2'-dioxy-4-pregnen-11β-ol-3,20-dione, a compound of claim 1.

7. 17α,21-Tetrahydropyranylidene-2',2'-dioxy-4-pregnen-11β-ol-3,20-dione, a compound of claim 1.

8. A pharmaceutical composition comprising an antiphlogistically effective amount of a compound of claim 1 and a pharmaceutically acceptable carrier.

9. A method of treating inflammation in a patient which comprises administering an antiphlogistically effective amount of a compound of claim 1 to the patient.

10. The method of claim 9, wherein the administration is topical.

* * * * *

UNITED STATES PATENT AND TRADEMARK OFFICE
CERTIFICATE OF CORRECTION

PATENT NO. : 4,264,584
DATED : April 28, 1981
INVENTOR(S) : Baumgarth et al.

It is certified that error appears in the above—identified patent and that said Letters Patent is hereby corrected as shown below:

Column 6, claim 1, formula reads:

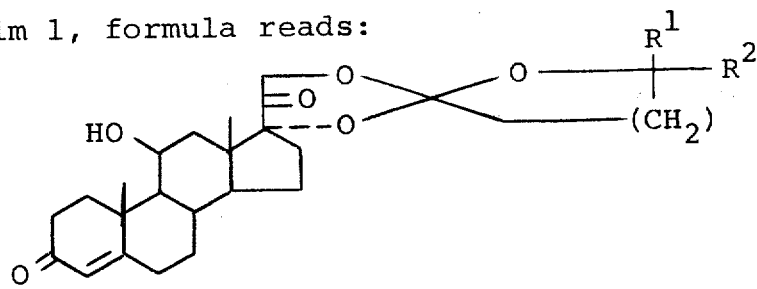

formula should read:

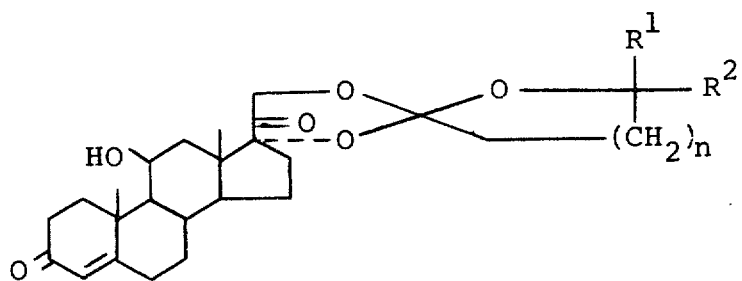

Signed and Sealed this

Eighth Day of September 1981

[SEAL]

Attest:

GERALD J. MOSSINGHOFF

Attesting Officer    Commissioner of Patents and Trademarks